(12) United States Patent
Guzorek

(10) Patent No.: US 6,679,068 B1
(45) Date of Patent: Jan. 20, 2004

(54) ULTRAVIOLET LAMP ASSEMBLY

(75) Inventor: Steven E. Guzorek, Kinston, NC (US)

(73) Assignee: Field Controls, L.L.C., Kinston, NC (US)

( * ) Notice: Subject to any disclaimer, the term of this patent is extended or adjusted under 35 U.S.C. 154(b) by 0 days.

(21) Appl. No.: 10/308,327

(22) Filed: Dec. 3, 2002

(51) Int. Cl.$^7$ .............................................. F25D 23/00
(52) U.S. Cl. ...................................... 62/78; 422/186.19
(58) Field of Search ................. 62/78, 264; 422/186.19

(56) References Cited

U.S. PATENT DOCUMENTS

| | | | | |
|---|---|---|---|---|
| 5,755,103 A | * | 5/1998 | Na et al. ......................... | 62/78 |
| 5,919,422 A | * | 7/1999 | Yamanaka et al. ........... | 422/121 |
| 5,987,908 A | * | 11/1999 | Wetzel ........................ | 62/259.1 |
| 6,372,186 B1 | * | 4/2002 | Fenci et al. .................. | 422/121 |
| 6,500,267 B1 | * | 12/2002 | Fenci et al. .................... | 134/1 |

* cited by examiner

Primary Examiner—Melvin Jones
(74) Attorney, Agent, or Firm—McDermott, Will & Emery

(57) ABSTRACT

There is provided a method and apparatus for an improved ultraviolet lamp assembly using an ultraviolet (UV) lamp with a sleeve having improved UV lamp temperature characteristics for improved UV lamp intensity output and germicidal affect. The ultraviolet lamp assembly comprises a UV lamp housed in a vented open end quartz sleeve in a portable air conditioning (AC) unit. The quartz sleeve comprises a distal sleeve open end and a proximal base open end through which a UV lamp is secured to the sleeve and AC unit. The proximal open end of the quartz sleeve comprises a plurality of venting slots that allow ambient air to travel into and out of the space between the UV lamp and the sleeve wall. Operation of the AC unit fan results in air flow into the sleeve at a proximal sleeve base end and out through the distal open end of the sleeve to thereby maintain the UV lamp at a desired temperature for improved germicidal affect.

25 Claims, 10 Drawing Sheets

ULTRAVIOLET LAMP ASSEMBLY

FIELD OF THE INVENTION

The present invention generally relates to an ultraviolet lamp assembly for killing germs or bacteria in air ventilation systems. Specifically, the present invention relates to an ultraviolet lamp including a quartz sleeve having a vented open end which results in increased or improved germicidal and bactericidal effect in systems and apparatus using ultraviolet lamps for purification or cleaning of air.

BACKGROUND OF THE INVENTION

The use of certain wave lengths of ultraviolet ("UV") light or radiation for its purification, germicidal and bactericidal effect is well known. UV light is commonly used to control the growth of and kill impurities in septic, water and air systems. For example, UV light or UV lamps are commonly used in heating, ventilation, and air conditioning ("AC" or "HVAC") systems for purification or air cleaning purposes. UV lamps are typically installed or mounted in the air ducts of AC systems in such a manner that the UV light emitted by the lamp floods the interior of the air duct. Air flowing through that duct will be irradiated with UV radiation which will have a germicidal or bactericidal affect on the moving air thereby reducing the impurities in the air flow.

A drawback of existing UV lamps in exiting UV lamp assemblies is that the UV lamps experience diminished UV radiation output intensity over time which results in reduced germicidal and bactericidal affect of the UV lamp cleaning device. Output from such UV lamps typically reaches its maximum rated output intensity after the first few minutes of operation, after an initial heat up period of the UV lamp. The UV lamp output then typically decreases over time to a generally steady lamp intensity output as the lamp continues to operate. The steady state output is about 20% less that the maximum output obtained during the first few minutes of UV lamp operation. The drop in UV lamp output intensity is typically due to the inconsistent and variable temperature around the UV lamp that does not allow proper and uniform UV lamp cooling. The diminished UV lamp output is even more pronounced when air or water is circulated around the lamp which causes a higher rate of cooling as is well know to those of skill in the art.

Moreover, inconsistent and variable air temperatures present around a standard UV lamp result in a cooling affect that does not allow proper and uniform UV lamp cooling. In the long term, this cooling effect can adversely affect the UV lamp's germicidal or bactericidal effect by causing the inside of the lamp to blacken or darken which in turn causes or results in a reduced UV lamp output intensity level.

In other typical UV lamp configuration, the UV lamp is mounted inside a quartz tube as an attempt to counteract known lamp-cooling issues or problems. However, such a configuration, when operated in still air, results in a larger drop in UV lamp intensity output than a standalone UV lamp. Output of a UV lamp covered by a quartz tube typically reaches its maximum rated output intensity after a few minutes of operation after the initial heat-up or warm-up period. Again, the UV lamp output will typically decrease to a generally steady lamp intensity output as the lamp continues to operate. In this configuration, the steady state output is about 35% less that the maximum output obtained during the first few minutes of UV lamp operation. Thus, the quartz outer tube results in a greater loss of UV lamp output intensity.

There is thus a need for an improved ultraviolet UV lamp assembly having improved UV lamp temperature characteristics for improved UV radiation intensity output for improved germicidal and bactericidal affect in purification, sterilization, cleaning or airflow systems.

SUMMARY OF THE INVENTION

The present invention provides a method and apparatus for an improved ultraviolet lamp assembly using an ultraviolet (UV) lamp with a vented quartz sleeve or tube having improved UV lamp temperature and cooling characteristics resulting in improved UV lamp intensity output for increased germicidal and bactericidal effect. The UV lamp assembly of the present invention can be used in systems and applications intended to purify, sterilize, clean and sanitize a medium, object or device. Further, the vented sleeve or tube is preferably a vented open end tube though other configurations may be used depending on a particular use application of the UV lamp assembly.

In one embodiment, the ultraviolet lamp assembly comprises a UV lamp housed in a vented open end quartz sleeve or tube in a portable air conditioning (AC) or heating unit. The quartz sleeve comprises a distal open end and a proximal open end. The UV lamp can be inserted into either end and secured to the tube, and the sleeve or tube is then secured to the AC or heating unit. The proximal open end of the quartz sleeve comprises a plurality of venting slots or ports that allow the air to travel into and out of the area or space between the UV lamp and the sleeve wall. The movement of air is preferably initiated by a fan or air displacer in the unit. Operation of the unit's fan results in air flow into the quartz sleeve at a proximal sleeve base end and out through the distal open end of the quartz tube. Air can also be drawn through the tube without operation of the fan by creating a "chimney" effect in the quartz tube from the heating of the air in the tube.

It is an object of the present invention to provide an ultraviolet lamp assembly that can he used in an AC or HVAC system for purification and cleaning of air flowing in the AC or HVAC system air ducts.

It is an object of the present invention to provide a UV lamp assembly with a vented quartz sleeve to provide improved and more consistent UV radiation intensity output.

It is an object of the present invention to provide a UV lamp assembly with a vented quartz sleeve with an open distal end to provide improved and more consistent UV radiation intensity output.

It is an object of the present invention to increase UV lamp life by producing more consistent and stable UV lamp temperature.

It is an object of the present invention to provide a UV lamp assembly with a vented quartz sleeve where the UV radiation intensity output is substantially uniform and constant when an associated AC fan is operating.

It is an object of the present invention to provide a shield or panel for the UV lamp assembly to improve and maintain the UV radiation intensity output of the UV lamp and where the shield or panel can be curved and extend to about 120 degrees.

It is an object of the present invention to provide a UV lamp assembly having an effective germicidal and bactericidal affect in a wavelength of about 254 nm.

It is an object of the present invention to provide a UV lamp assembly where the air around a UV lamp can be maintained in the range of 80° F. to 100° F. for improved germicidal and bactericidal affect in an air purification system.

It is an object of the present invention to provide an ultraviolet lamp assembly that can be used to purify air in an airflow system such as an air conditioning system in a home, hotel or building.

It is an object of the present invention to provide an ultraviolet lamp assembly that can be used to purify air in an airflow system such as a portable or standalone air conditioning unit.

The following drawings and description set forth additional advantages and benefits of the invention. More advantages and benefits will be obvious from the description and may be learned by practice of the invention.

BRIEF DESCRIPTION OF THE DRAWINGS

The present invention may be better understood when read in connection with the accompanying drawings, of which.

DETAILED DESCRIPTION

Figure 1:
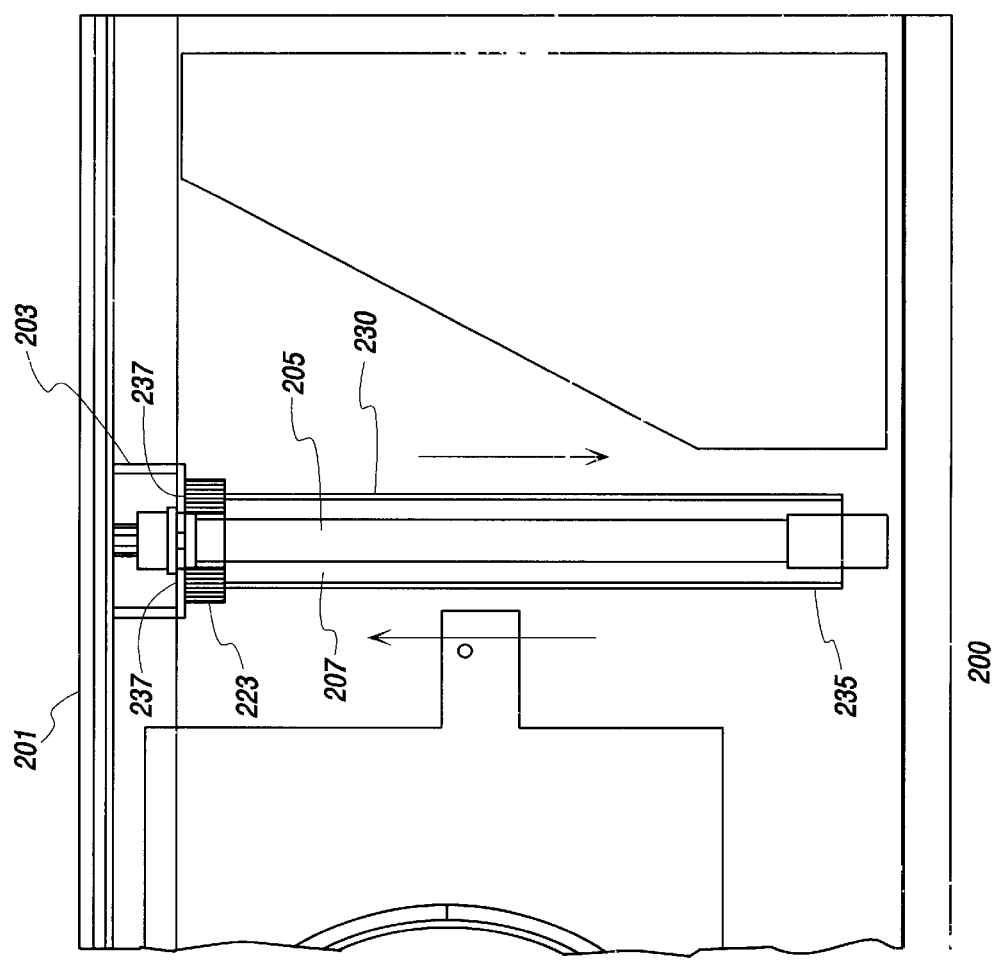
FIG. 1 illustrates a novel ultraviolet lamp assembly positioned on a portion of a housing of a portable air conditioning unit in accordance with an embodiment of the present invention.

FIG. 1 shows an embodiment of a novel ultraviolet lamp assembly 200 positioned and secured to a portion of a housing 201 of a portable air conditioning unit (shown in FIG. 7) in accordance with the present invention. The UV lamp assembly 200 preferably comprises a UV lamp 205 and a quartz tube or sleeve 230 with a proximal base end 203 having a plurality of venting ports or slots 237 and an open distal end 235. The ultraviolet (UV) lamp 205 preferably has a bandwidth of about 240 nm to 360 nm for best germicidal and bactericidal affect. Other bandwidths outside this range or a specific wavelength within the range may be used for specific desired applications. In the preferred embodiment, the UV lamp 205 is an ozone free UV lamp which is operatively housed in the elongated sleeve or tube 230. However, other types of lamps and lamp configurations may be used and the assembly may have one or more UV lamps 205. The quartz sleeve 230 will preferably have complimentary physical configurations to accommodate and house one or more UV lamps 205 having other shapes and sizes. The ultraviolet lamp assembly 200 can also be used in other cleaning or purification systems that are not portable and have extensive air ducts.

Figure 5:
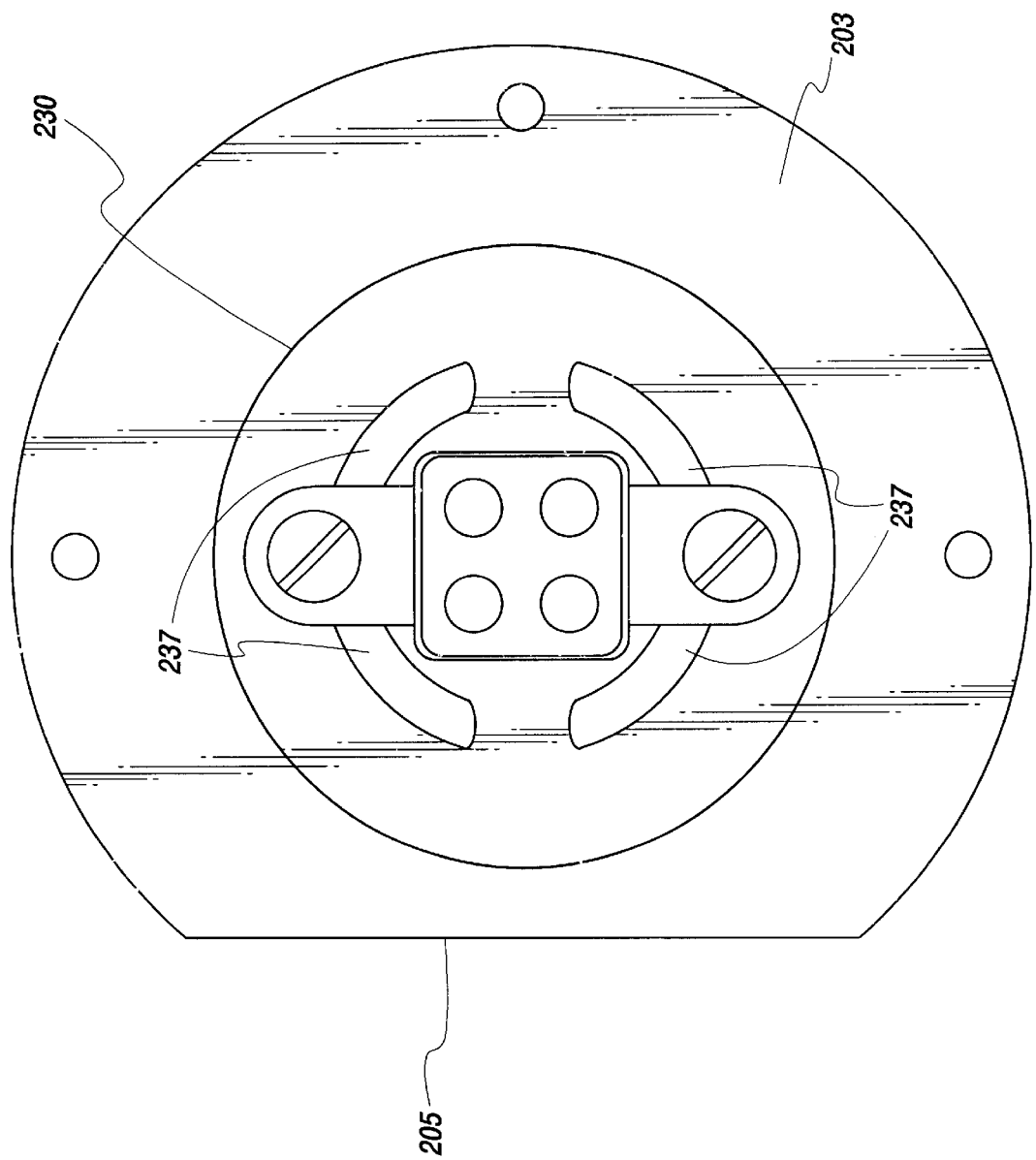
FIG. 5 illustrates a sleeve base of the ultraviolet lamp assembly of FIG. 4 showing a plurality of venting slots according to an embodiment of the present invention.

The sleeve 230 is preferably an elongated hollow tube with a proximal end 223 (also shown in FIG. 5). The sleeve or tube 230 is preferably comprised of a quartz material, however other suitable UV transparent materials may used to make up the sleeve 230. The proximal end 223 preferably has a base 203 connected to the tube 230 and is configured such that the UV lamp 205 can be inserted into the quartz sleeve 230 and secured to the base 203. Further, the base 203 preferably comprises a plurality of venting orifices, air vents, slots or ports 237. In the embodiment shown, there are four venting slots 237 (shown in FIG. 5), however those of skill in the art will readily recognize that the number of venting orifices 237 may be more or less depending on the particular application where the UV lamp assembly 200 is to be used. The plurality of venting orifices or ports 237 in the base 203 and the distal open end 235 enable or allow air to enter and/or exit the quartz sleeve 230, i.e., to travel into or out of a space 207 that is formed between the UV lamp 205 and the quartz sleeve 230.

The UV lamp 205 is preferably positioned and secured to the sleeve 230 at the proximal open end 223 of the sleeve 230 (also shown in FIG. 5). When the UV lamp 205 is operatively positioned in the sleeve 230 there is a space 207 between the UV lamp's 205 outer or exterior surface and the interior surface or wall of the sleeve 230 is formed and created. The venting slots 237 in the sleeve base 203 and the distal open end 235 form an airflow pathway for air to enter and exit the quartz sleeve 230 and to move in the air space 207 between the UV lamp 205 and the quartz sleeve 230. This will allow circulation of air or air flow through the interior of the quartz sleeve 220 from venting slots 237 to distal end 235 or in the opposite direction from distal open end 235 to venting slots 237. The flow of air or other selected medium allows the appropriate, consistent and uniform cooling of the UV lamp during operation of the lamp. In this manner, the UV lamp output intensity can be maintained at a higher level for a longer period of time and thus increase the germicidal and bactericidal effect of the UV lamp.

Figure 2:
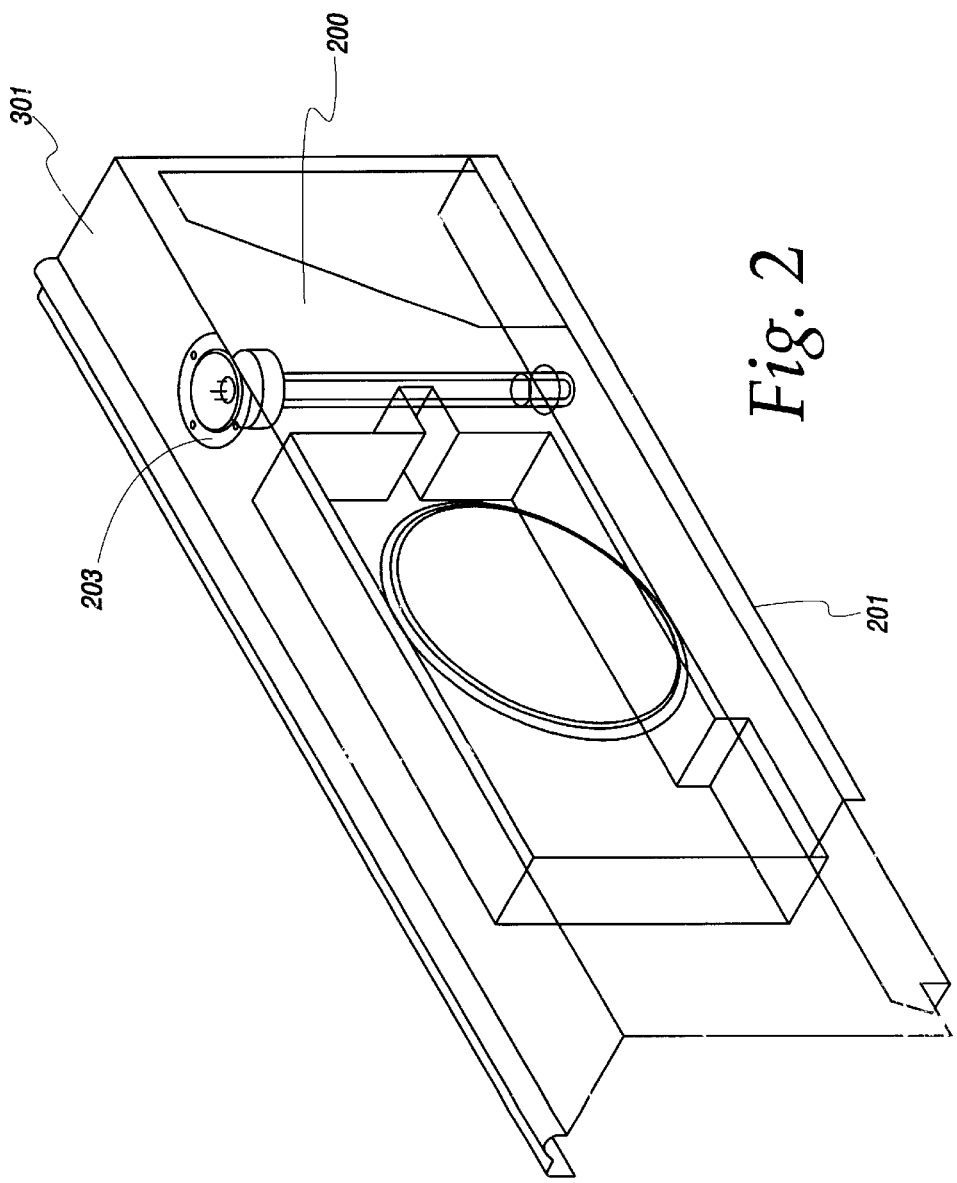
FIG. 2 illustrates an isometric view of the ultraviolet lamp assembly of FIG. 2 on the housing of a portable air conditioning unit.
Figure 3A:
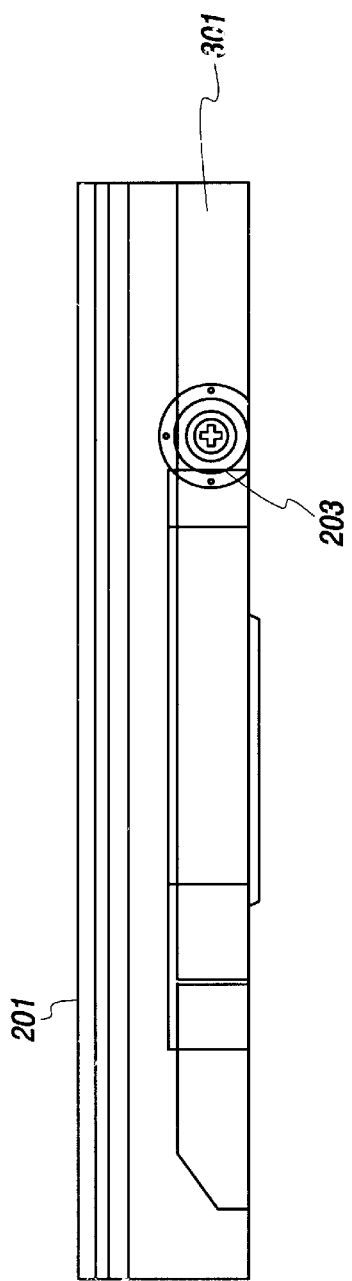
FIG. 3A illustrates a top view of the housing and ultraviolet lamp assembly of FIGS. 2 and 3.
Figure 3B:
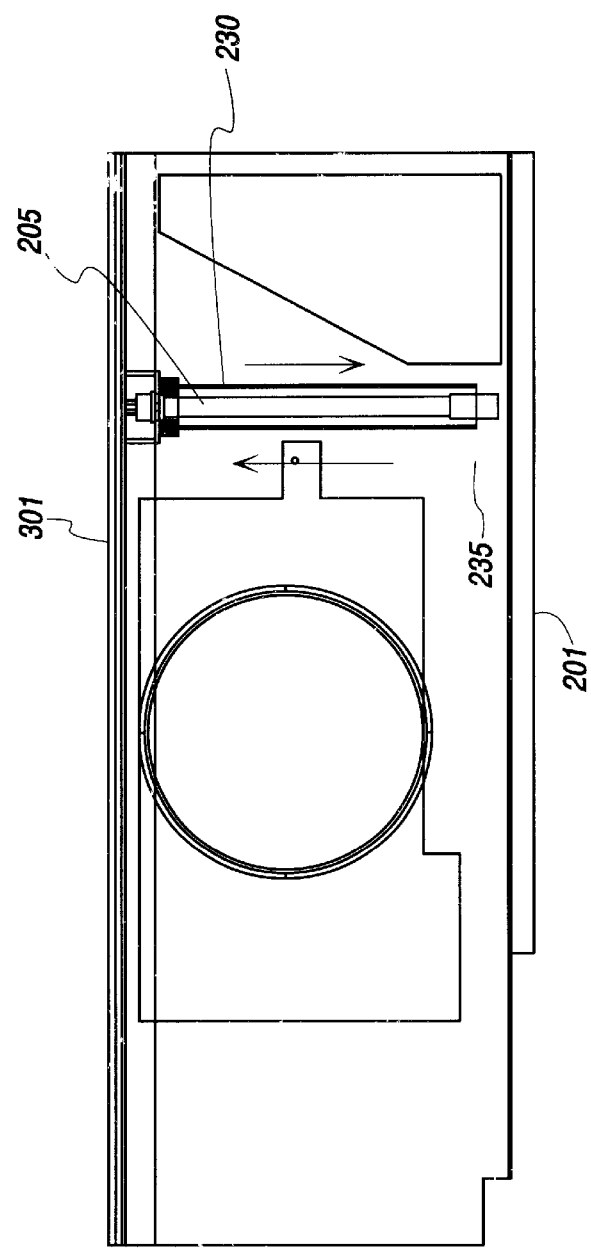
FIG. 3B illustrates a rear view of the housing and the ultraviolet lamp assembly of FIGS. 1 and 2.
Figure 7:
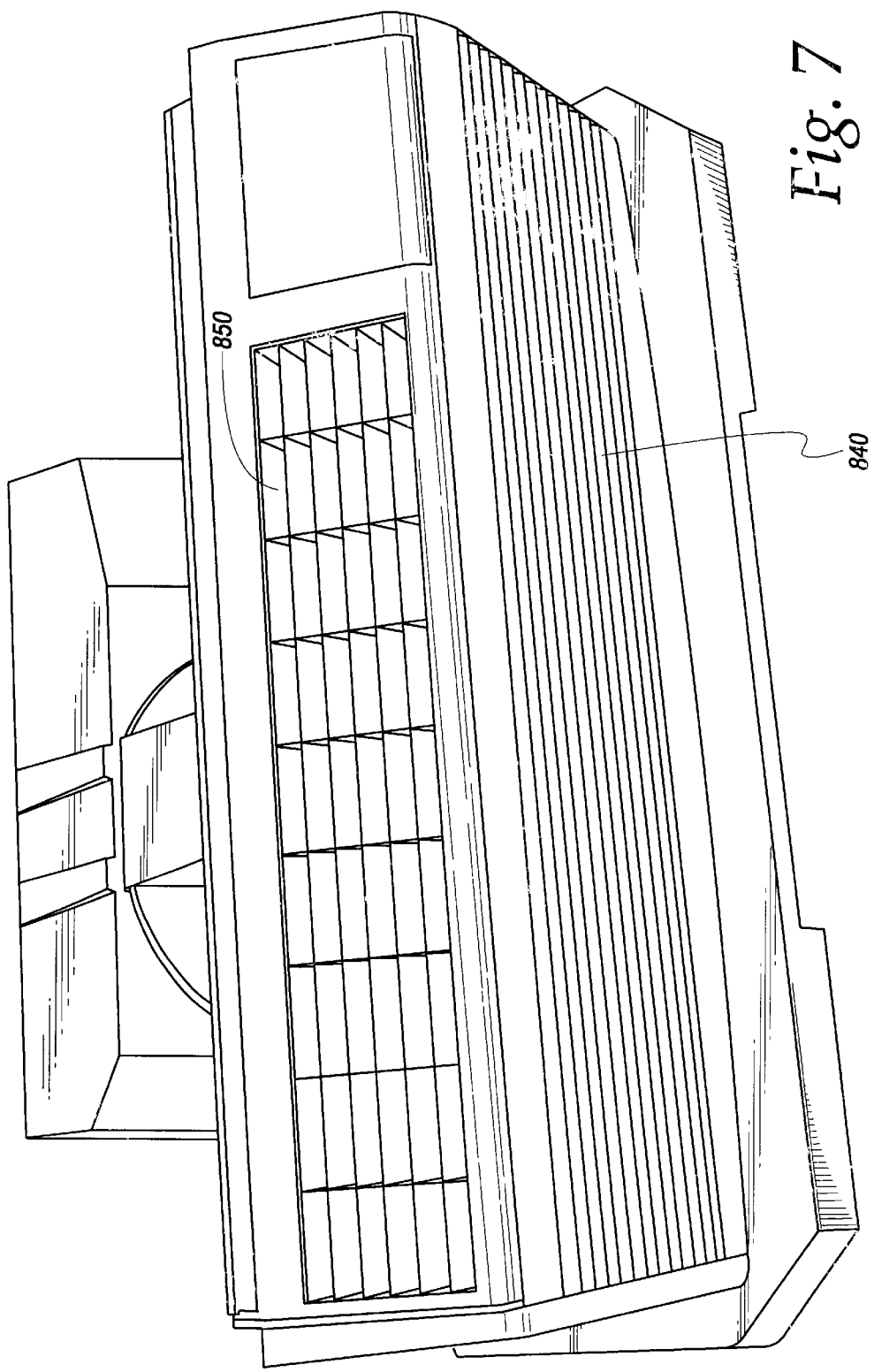
FIG. 7 illustrates an air conditioning unit where the ultraviolet lamp assembly of FIGS. 1 and 4 could be used.
Figure 8:
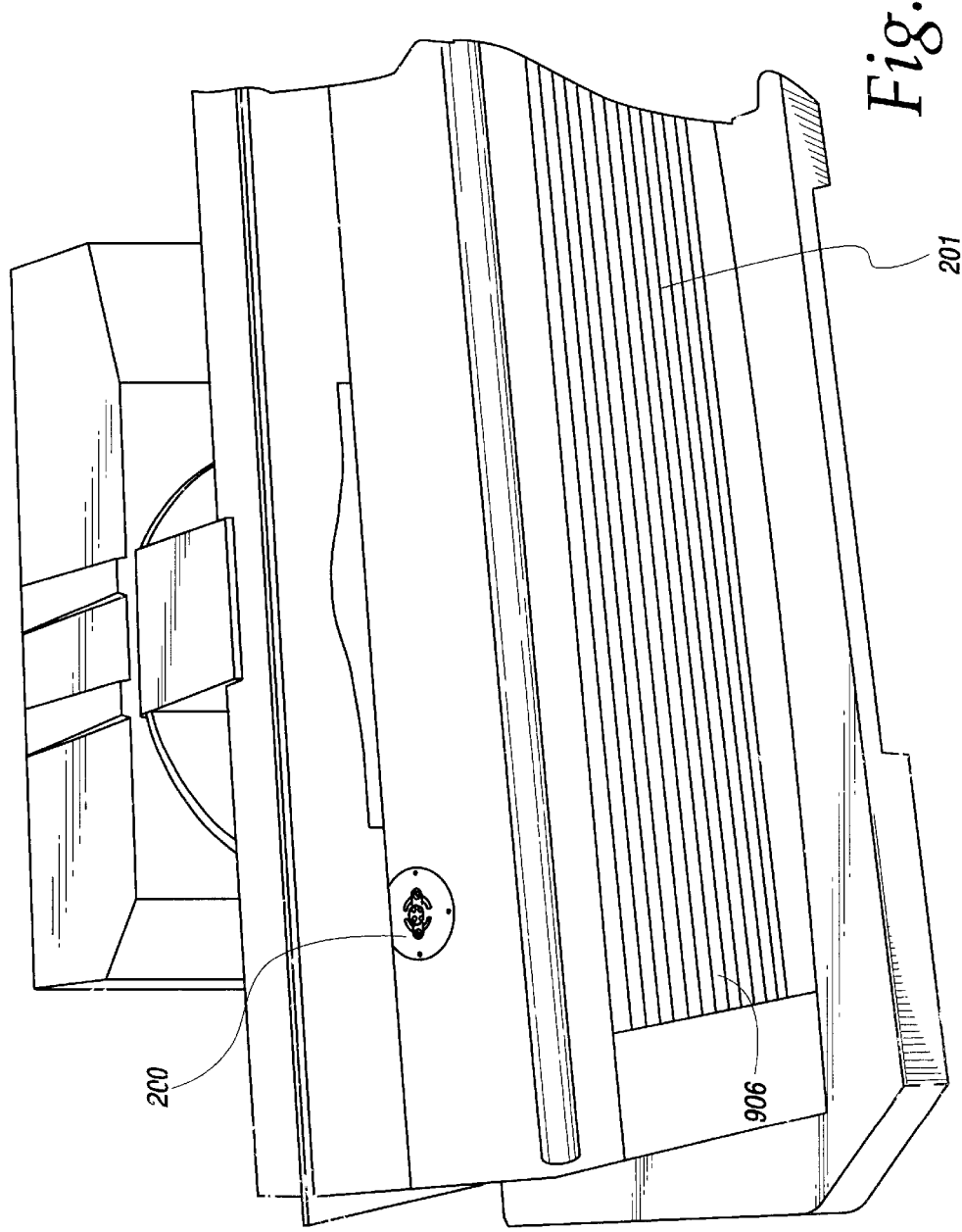
FIG. 8 illustrates the air conditioning unit with the ultraviolet lamp assembly of FIG. 4 mounted therein according to an embodiment of the present invention.

FIG. 2 shows an isometric view of a preferred embodiment of the ultraviolet lamp assembly 200 shown in FIG. 2 positioned on a panel or housing 201 which can be mounted in the interior of a portable air conditioning unit 800 (shown in FIGS. 7 and 8). The AC unit 800 can be a typical portable appliance or device that may perform the functions of cooling and/or heating air. Such a device may be located in a window or in a wall for circulation of ambient room air. FIGS. 3A and 3B shown top and rear views of the housing 201 and ultraviolet lamp assembly 200 of FIG. 2. As shown, the UV lamp assembly 200 is preferably secured to a top portion 301 of the housing 201 at the base end 203 such that the UV lamp 205 and the quartz sleeve 230 extend vertically downward from the top 301 and in front of the housing 201. (also shown in FIG. 4)

Figure 4:
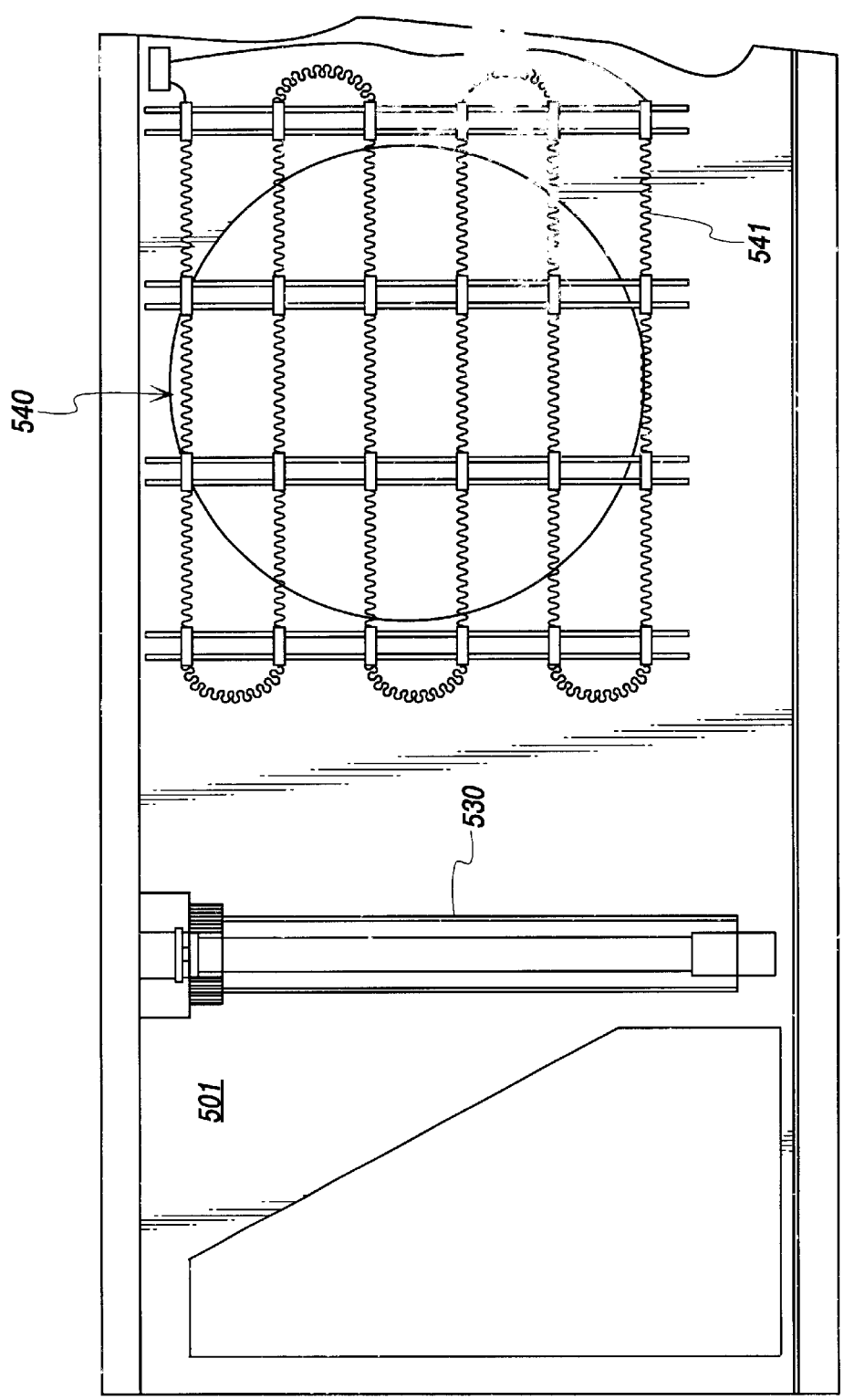
FIG. 4 illustrates an ultraviolet lamp assembly positioned on a housing of a portable air conditioning unit in accordance with another embodiment of the present invention.

FIG. 4 further shows that the UV lamp assembly 200 is preferably mounted on the front side of the housing 301. Those of skill in the art will readily recognize that the UV lamp assembly can be mounted in other desired or appropriate locations of the housing 301 or portable AC unit 800.

Figure 6:
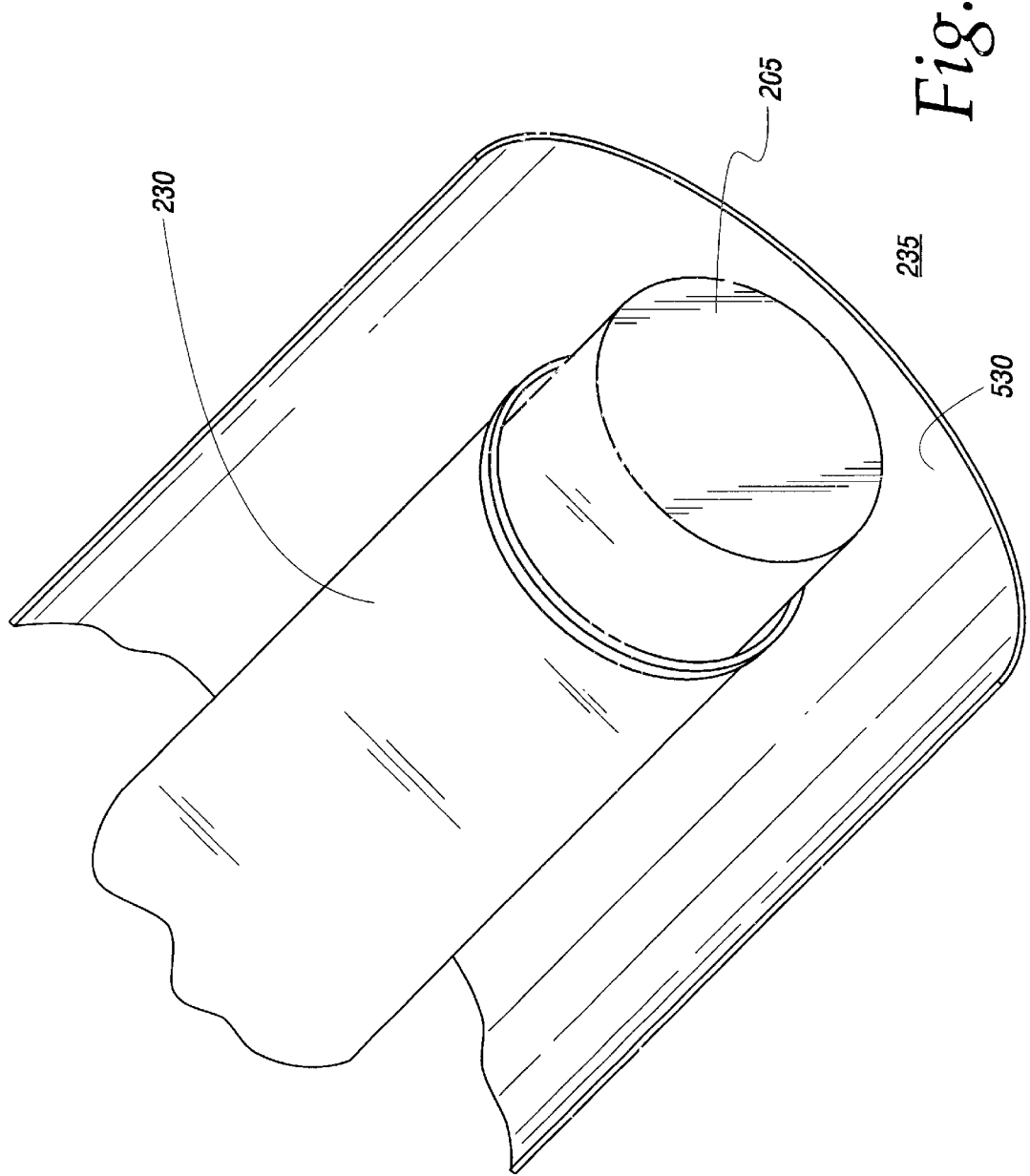
FIG. 6 illustrates a sleeve distal open end and a shield of the ultraviolet lamp assembly of FIG. 4.

In an alternate embodiment, the UV lamp assembly 200 further comprises a shield or panel 530 that is preferably configured to extend from approximately the base 203 to the distal end 235 and is curved lengthwise to cover approximately half of the quartz sleeve 230 (shown in FIGS. 4 and 6). The shield or panel can be curved from about 120 to 180 degrees. Further, the shield is preferably positioned between the housing wall 501 and the quartz sleeve 230. The shield or panel 530 can deflect or direct the UV radiation in a desired direction. The shield or panel can also serve to protect the housing wall 501 which may contain plastic parts, from degradation to the generated UV radiation. Those of skill in the art will readily recognize that whether or not a shield or panel 530 is used will depend on the particular application of where the UV lamp assembly 200 is to be used and components or objects in the vicinity of the UV lamp assembly 200 UV radiation, such as the housing wall 501.

FIG. 5 shows in more detail the proximal end 223 of the quartz sleeve 230 and particularly the plurality of venting slots or ports 237 in the base 203. It also show how the UV lamp 205 is mounted to the base 203 in this embodiment. FIG. 6 shows in more detail the distal open end 235 of the quart sleeve 230, as well as a bottom portion of the curved shield or panel 530 that is used in some embodiments to redirect UV radiation and/or to protect surrounding material and components from UV radiation. Together, the venting ports or slots 237 and the distal open end 235 provide or define an airflow path to enable or allow air to enter and exit the quartz sleeve 230 and to travel in the space 207 between the UV lamp 205 and the quartz sleeve 230.

Figure 9:
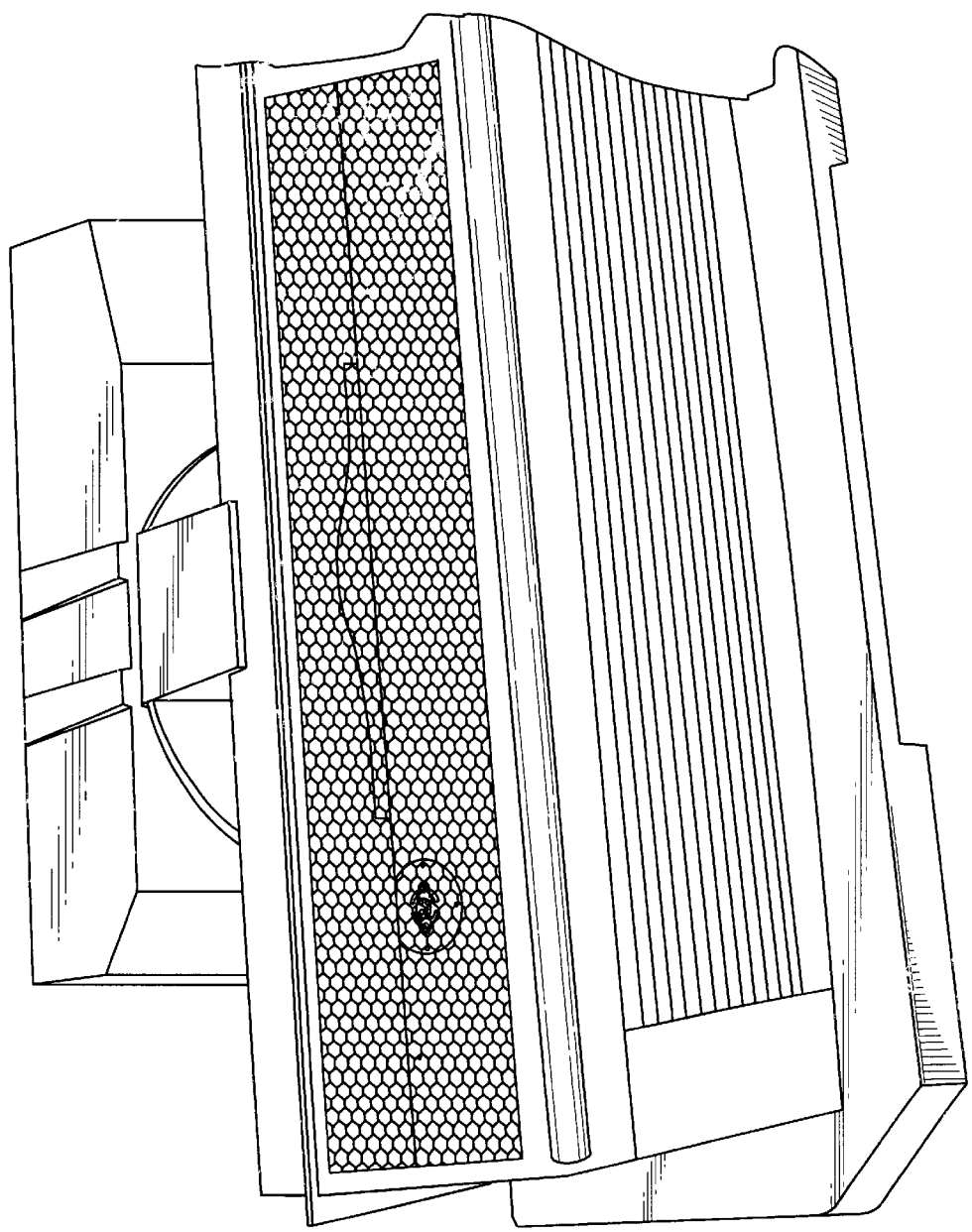
FIG. 9 illustrates the air conditioning unit of FIG. 8 with a fan guard positioned above the ultraviolet lamp assembly of FIG. 4.
Figure 10:
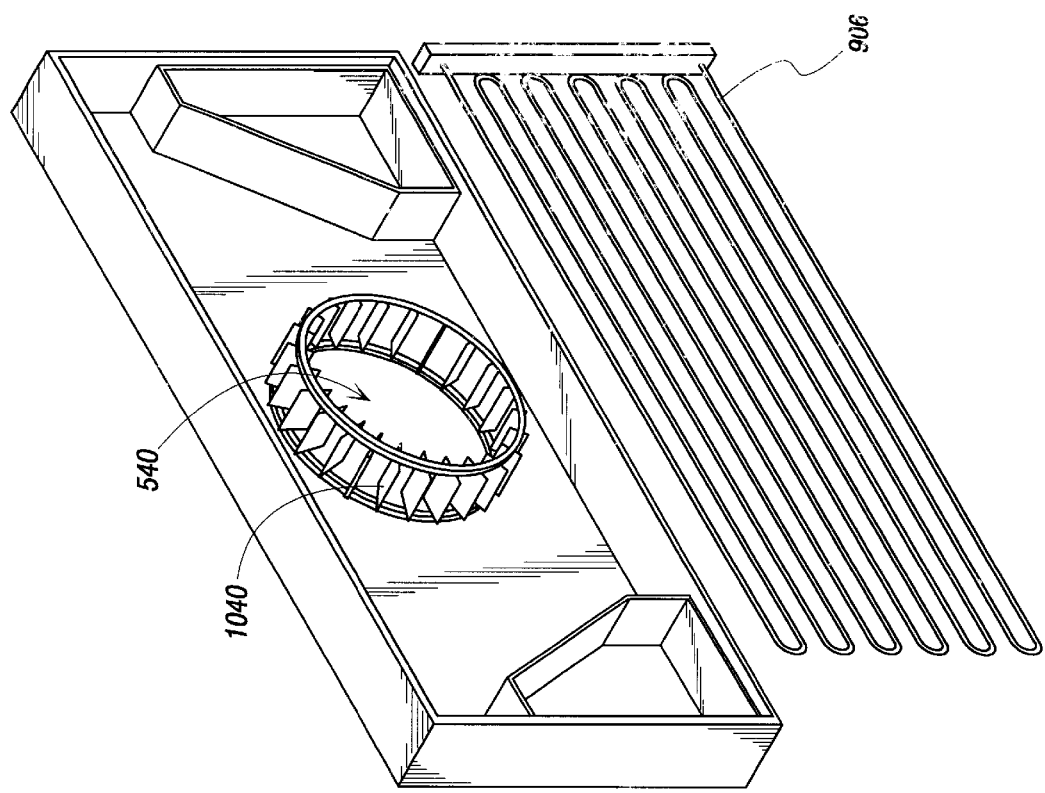
FIG. 10 illustrates a circulation fan that could be used with the air conditioning unit of FIG. 7 to circulate air in the ultraviolet lamp assembly of FIG. 4.

FIGS. 7–10, illustrate an air conditioning unit 800 where embodiments of the ultraviolet lamp assembly 200 may be mounted and used, preferably in the interior of an AC unit 800. The AC unit 800 may be a portable appliance and it can be a device that performs the functions of cooling and/or heating air. Such a device may be located in a room, window or in a wall for circulation of ambient room air, or could be part of a larger air conditioning system. FIG. 7 further shows the preferred position of the UV lamp assembly 200 in the AC unit 800 in this embodiment. FIG. 8 shows that, in the AC unit 800 of FIG. 8, the UV lamp assembly 200 of FIGS. 1–4 is preferably mounted inside the AC unit 800 and between the AC coils 906 and the unit circulation fan 1040 (shown in FIG. 10). FIG. 9 further shows that a fan guard is preferably mounted above the UV lamp assembly 200 and housing 201. This can be for safety purposes and/or to keep debris out the area above the UV lamp assembly 200.

In operation, the UV lamp assembly 200 is preferably mounted or positioned in a housing 201 (FIGS. 1, 2, 3A, 3B and 4) in the interior of a portable air conditioning unit 800 (FIG. 7). The UV lamp assembly 200 is preferably secured to the top portion 301 (shown in FIGS. 2, 3A and 8) and positioned in front of the housing 301 (shown in FIG. 4). The housing 201 with the attached UV lamp assembly 200 is positioned inside the AC unit 800 (shown in FIGS. 8 and 9) and adjacent to or in front of the AC coils 906 (shown in FIGS. 8 & 9). Cooperatively positioned adjacent to the rear of the housing 201 is a circulation fan 1040 (shown in FIG. 10) that, when in operation, will pull ambient air from a room or other designated air source. When the circulation fan 1040 is operating, the ambient air is pulled from the area outside the front grill or cover 840 of the AC unit 800 and into the AC unit. The intake ambient air passes the UV lamp assembly 200, the AC coils 906 and a heater strip 541 that, in this embodiment, is mounted to the front of the housing 201. The intake ambient air then travels or flows through a fan intake orifice 540 (shown in FIGS. 2, 3B and 4). Once the intake ambient air passes the fan intake orifice 540, the air is forced or routed upward toward the top of the AC unit 800 where the air exits the AC unit 800 through exit vents 850 (FIG. 7).

The air that exits the AC unit 800 via the exit vents 850 will either be hotter or colder as compared to the air entering the AC unit 800 via the front AC unit cover 840 depending on the unit's 800 mode of operation. If the AC unit 800 was in heater mode, then the air exiting the AC unit 800 will be heated by the heater strip 541 as the air passes into the fan intake orifice 540. If the AC unit 800 was in cooling mode, then the air exiting the AC unit will be cooled by the AC coils 906 as the air passes toward the fan intake orifice 540.

During operation of the circulation fan 1040, a portion of the air the being routed or expelled out through the AC exits vents 850 may be diverted through the UV lamp assembly 200. During operation of the intake circulation fan 1040, the front area of the housing 201 is at a negative pressure relative to the top 301 rear part of the housing 201 where the air that was sucked in by the circulation fan is being expelled. There is thus a negative pressure at the distal open end 235 of the sleeve 230. At the same time, there is a higher positive pressure at the proximal base 203, which has the venting slots 237, positioned at the top 301 of the housing 201. As noted previously, the proximal base venting slots 237 and the distal open end 235 of the sleeve 230 form a path or conduit for airflow. And, since the area above the proximal base venting slots 237 is at a higher or positive pressure and the sleeve distal open end 235 is at a negative pressure relative to venting slots, a portion of the air exiting the AC unit may be sucked, funneled or forced to travel into the sleeve 230 due to the pressure difference. The air will travel in the space 207 between the UV lamp 205 and the sleeve 230 from the venting slots 237 downward and out at the distal open end 235 into the area in front of the housing 201. The air will then join air that is being pulled through the fan intake 540 and circulate as just described.

The air traveling through the sleeve 230 as a result of the pressure differential created by the intake circulation fan 1040, as just described, preferably produces a cooling air flow in the UV lamp assembly 200 inside the quartz sleeve 230 that enables the UV lamp 205 maintain a consistent temperature and/or to control the temperature in the space 207 between the UV lamp 205 and the sleeve 230. This will allow the UV lamp intensity output to be maintained near its maximum output. The improved UV intensity output will allow the UV lamp assembly 200 to provide an improved germicidal and bactericidal affect. This will enable a system that uses the UV lamp assembly to better purify the ambient air and, as a result, a portable air conditioning system using such a UV assembly 200 will able to provide cleaner air. For a UV lamp operating at a wavelength of 254 nm, the temperature around the lamp is preferably maintained in the range of about range of 80° F. to 100° F. for consistent and improved germicidal and bactericidal affect on the air in the AC unit 800. Those of skill in the art will readily recognize that the preferred temperature will depend on the rated output intensity and length of the UV lamp 205 uses in the UV lamp assembly 200. In one embodiment, the preferred temperature is 90° F. for a UV lamp 205 operating at a 254 nm wavelength for optimum germicidal affect on the ambient air in the AC unit 800.

The invention has been described and illustrated with respect to certain preferred embodiments by way of example only. Those skilled in that art will recognize that the preferred embodiments may be altered or amended without departing from the true spirit and scope of the invention. Therefore, the invention is not limited to the specific details, representative devices, and illustrated examples in this description. The present invention is limited only by the following claims and equivalents.

I claim:

1. An air conditioning apparatus comprising:

a means for heating or cooling ambient air;

a housing comprising an air intake section;

an ultraviolet lamp assembly operatively positioned on said housing,
said ultraviolet lamp assembly comprising,
an ultraviolet lamp,
a sleeve having a proximal sleeve base portion, a generally cylindrical portion positioned around said ultraviolet lamp and an open distal end,
said cylindrical portion of said sleeve and said ultraviolet lamp defining a space therebetween,
said sleeve base portion having a vent port therein,
said vent port providing a passage to said space between said sleeve and said ultraviolet lamp;
a circulation fan operative to move ambient air through said housing;
whereby operation of said circulation fan creates a negative pressure at said open distal end of said sleeve relative to said vent port thereby resulting in airflow into said space between said sleeve and said ultraviolet lamp.

2. The air conditioning apparatus of claim 1 wherein said ultraviolet lamp assembly further comprises a shield cooperatively attached adjacent to said sleeve.

3. The air conditioning apparatus of claim 2 wherein said shield has a curved configuration that extends substantially parallel along said sleeve.

4. The air conditioning apparatus of claim 1, wherein said ultraviolet lamp is an ozone generating or ozone free ultraviolet lamp.

5. The air conditioning apparatus of claim 1, wherein said sleeve is a quartz sleeve.

6. The air conditioning apparatus of claim 2, wherein said ultraviolet lamp emits radiation at a wavelength of 254 nm.

7. The air conditioning apparatus of claim 6, wherein said airflow of air in said space is able to maintain air around said ultraviolet lamp at about 90° F.

8. An ultraviolet lamp assembly for emission of radiation having a germicidal or bactericidal affect comprising:
an ultraviolet lamp;
a sleeve having an open end, said sleeve substantially covering said ultraviolet lamp and creating a space between said ultraviolet lamp and said sleeve;
a mounting base, said ultraviolet lamp and said sleeve being mounted to said mounting base, said mounting base having at least one vent port communicating with said space between said ultraviolet lamp and said sleeve.

9. The ultraviolet lamp assembly of claim 8, further comprising a shield attached to said mounting base.

10. The ultraviolet lamp assembly of claim 9, wherein said shield has a curved configuration that extends substantially parallel along said sleeve.

11. The ultraviolet lamp assembly of claim 8, wherein said mounting base vent port and said open end of said sleeve together facilitate movement of air through said space between said ultraviolet lamp and said sleeve.

12. The ultraviolet lamp assembly of claim 8, wherein said ultraviolet lamp is an ozone generating or ozone free ultraviolet lamp.

13. The ultraviolet lamp assembly of claims 8, wherein said sleeve is a quartz sleeve.

14. The ultraviolet lamp assembly of claim 9, wherein said ultraviolet lamp emits radiation at a wavelength of 254 nm.

15. The ultraviolet lamp assembly of claim 14, wherein said air movement in said space is able to maintain air around said ultraviolet lamp temperature in a range of about 80° F. to 100° F.

16. The ultraviolet lamp assembly of claim 14, wherein said air movement in said space is able to maintain air around said ultraviolet lamp at about 90° F.

17. A method of maintaining a desired ultraviolet lamp temperature in an ultraviolet lamp assembly comprising the steps of:
disposing an ultraviolet lamp assembly in an air conditioning apparatus, said ultraviolet lamp assembly comprising a sleeve substantially covering said ultraviolet lamp, and a mounting base for mounting said ultraviolet lamp and said sleeve, said mounting base having a mounting base port therein;
operating a means for moving ambient air into and out of said air conditioning apparatus;
said means for moving ambient air, creating a pressure difference between a distal open sleeve end and said mounting base port, wherein said distal open sleeve end is adjacent to an air intake section of said air conditioning apparatus and said mounting base port is adjacent to an exit vent of said air conditioning apparatus thereby creating a negative pressure at said distal open sleeve end relative to said mounting base port; and
circulating a portion of said moving ambient air exiting at said exit vent into said sleeve via said mounting base port and out at said distal sleeve open end;
thereby maintaining said ultraviolet lamp at said desired temperature for improved germicidal affect of said ultraviolet lamp on said ambient air being moved into and out of said air conditioning apparatus.

18. The method of claim 17 wherein said air conditioning apparatus comprises:
a means for heating or cooling ambient air;
a housing comprising an air intake section;
a circulation fan operative to move ambient air through said air intake section and through exit vents of said air conditioning apparatus; and
wherein said ultraviolet lamp assembly is operatively positioned on said housing.

19. The method of claim 18 wherein:
said sleeve is configured to house said ultraviolet lamp therein, resulting in an air space between said ultraviolet lamp and said sleeve; and
said mounting base port comprising at least one vent port and adapted to mount said ultraviolet lamp assembly to said housing.

20. The method of claim 19 wherein said ultraviolet lamp assembly further comprises a shield cooperatively attached to said mounting base.

21. The method of claim 20 wherein said shield has a curved configuration that extends substantially parallel along said sleeve.

22. The method of claim 17, wherein said ultraviolet lamp is an ozone generating or ozone free ultraviolet lamp.

23. The method of claim 17, wherein said sleeve is a quartz sleeve.

24. The method of claim 17, wherein said ultraviolet lamp emits radiation at a wavelength of 254 nm.

25. The method of claim 17, wherein said portion of said moving ambient air is able to maintain air around said ultraviolet lamp at about 90° F.

* * * * *